(12) United States Patent
Dziewiszek et al.

(10) Patent No.: US 8,900,859 B2
(45) Date of Patent: Dec. 2, 2014

(54) CELL HOMOGENATE FROM STEM CELLS DERIVED FROM GROWING DEER ANTLERS, A METHOD OF OBTAINING IT AND ITS USE

(75) Inventors: Wojciech Dziewiszek, Wroclaw (PL); Marek Cegielski, Wroclaw (PL); Marek Bochnia, Wroclaw (PL)

(73) Assignee: Stem Cells Spin S. A., Wroclaw (PL)

( * ) Notice: Subject to any disclaimer, the term of this patent is extended or adjusted under 35 U.S.C. 154(b) by 113 days.

(21) Appl. No.: 13/574,553

(22) PCT Filed: Jan. 26, 2011

(86) PCT No.: PCT/PL2011/050003
§ 371 (c)(1),
(2), (4) Date: Aug. 30, 2012

(87) PCT Pub. No.: WO2011/093732
PCT Pub. Date: Aug. 4, 2011

(65) Prior Publication Data
US 2013/0004583 A1    Jan. 3, 2013

(30) Foreign Application Priority Data

Jan. 26, 2010 (PL) .......................... 390272
Jan. 24, 2011 (PL) .......................... 393720

(51) Int. Cl.
| | | |
|---|---|---|
| C12N 5/00 | (2006.01) | |
| C12N 5/02 | (2006.01) | |
| A61K 31/74 | (2006.01) | |
| A61K 35/12 | (2006.01) | |
| A61K 35/32 | (2006.01) | |

(52) U.S. Cl.
CPC ..................................... *A61K 35/32* (2013.01)
USPC .................. 435/325; 424/78.03; 424/520

(58) Field of Classification Search
CPC ... A61K 38/1709; A61K 38/17; C12N 12/85; C12N 5/0696; C12N 5/0018; C12N 5/0602; C12N 5/0603; C12N 5/0621; C12N 5/0671; C12N 5/0672; G01N 33/6893; G01N 33/5005; G01N 33/5058
See application file for complete search history.

(56) References Cited

U.S. PATENT DOCUMENTS

| | | | |
|---|---|---|---|
| 2007/0026084 A1* | 2/2007 | Coates et al. .................. | 424/520 |
| 2010/0041595 A1* | 2/2010 | Birr et al. ........................ | 514/12 |
| 2010/0184217 A1* | 7/2010 | Cegielski et al. .............. | 435/377 |

FOREIGN PATENT DOCUMENTS

WO    WO 2008/133536 A2    11/2008

OTHER PUBLICATIONS

Baciut, G. et al., "Study of deer antler as a potential bone regenerating biomaterial", International Journal of Oral and Maxillofacial Surgery, 2007, vol. 36, No. 11.

Cegielski, M. et al., "Experimental application of xenogenous antlerogenic cells in replacement of auricular cartilage in rabbits", Xenotransplantation, 2008, vol. 15, No. 6.

Pan, H.C. et al., "Post-injury regeneration in rat sciatic nerve facilitated by neurotrophic factors secreted by amniotic fluid mesenchymal stem cells", Journal of Clinical Neuroscience, 2007, vol. 14, No. 11.

International Search Report issued by the International Searching Authority (ISA/O.E.P.M.) on Apr. 20, 2011 in connection with International Application No. PCT/PL2011/050003.

* cited by examiner

*Primary Examiner* — Chris R Tate
*Assistant Examiner* — Douglas F White
(74) *Attorney, Agent, or Firm* — Gary J. Gershik; Cooper & Dunham LLP

(57) ABSTRACT

The subject of the present invention is a bioactive cell homogenate produced from cells belonging to the MIC-1 stem cell line derived from growing deer antlers (Cervidae) deposited at the DSMZ under the accession DSM ACC2854, a method of producing and using it. The present invention also encompasses a pharmaceutical or cosmetic composition containing the above-mentioned homogenate.

11 Claims, 10 Drawing Sheets

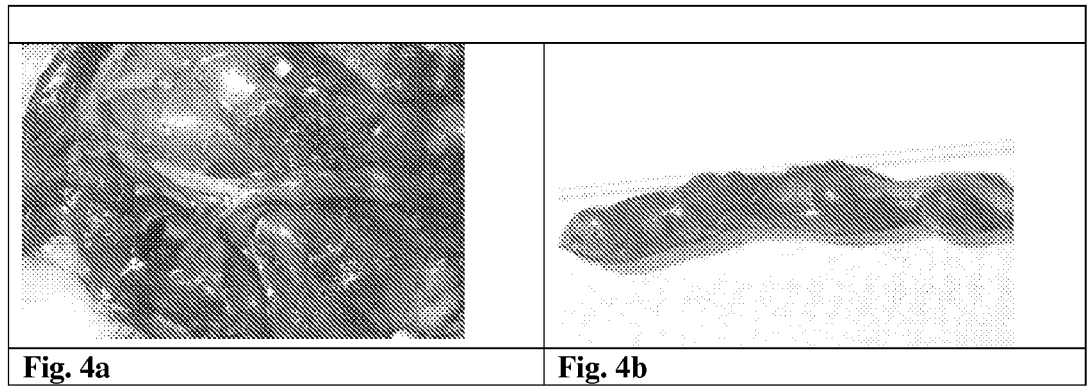
Fig. 4a | Fig. 4b
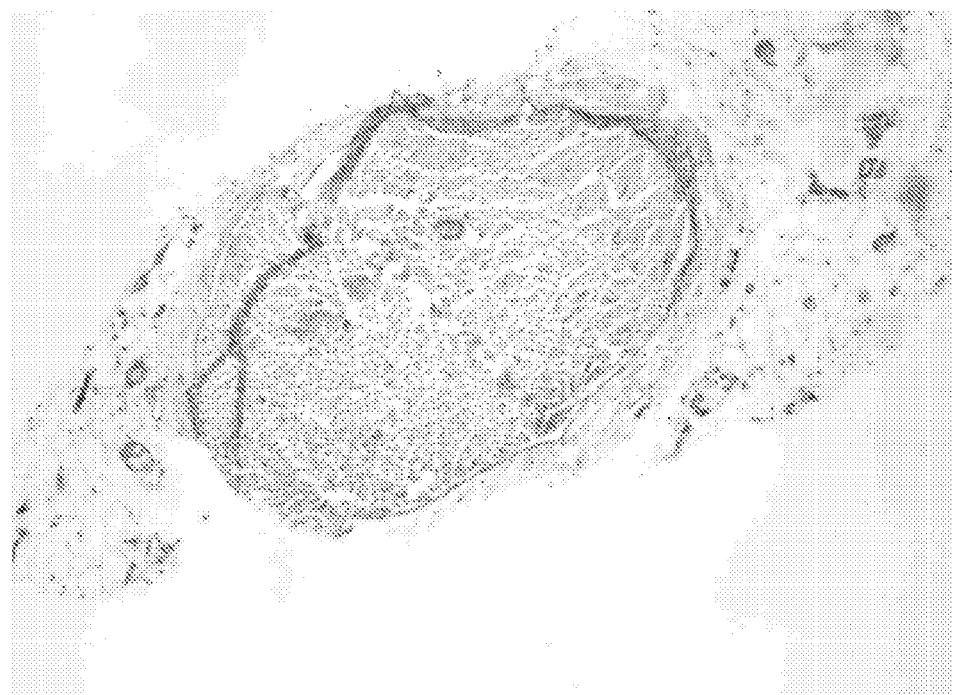
Fig. 5

CELL HOMOGENATE FROM STEM CELLS DERIVED FROM GROWING DEER ANTLERS, A METHOD OF OBTAINING IT AND ITS USE

This application is a §371 national stage application of PCT International Application No PCT/PL2009/050003, filed Jan. 26, 2011, the contents of all of which are hereby incorporated by reference into this application.

The subject of the present invention is a cell homogenate obtained from stem cells from growing deer antlers, a method of obtaining it and its use. The subject of the present invention is also a pharmaceutical or cosmetic composition containing the above-mentioned cell homogenate.

There have been many known attempts in the state of the art to isolate and produce stable stem cell lines, from which it would be possible to make stable preparations for various uses.

The disclosed solutions relating to obtaining stem cells that differentiate into osteoblasts are derived solely from various types of human tissue. Applications WO 2005/085422 and US 2005/0048644 disclose stem cells isolated from adipose tissue used in the treatment of muscle and skeletal diseases. Application W0 2005/038012 discloses a method of obtaining stem cells capable of differentiating into osteoblasts or chondroblasts from human postnatal tissue. Application US 2007/0122902 discloses a method of isolating and culturing multipotent stem cells obtained from umbilical blood. Attempts have also been made to genetically modify cells capable of regenerating cartilage and bone tissue, which were disclosed in patent description U.S. Pat. No. 6,398,816. The greatest ethical controversy concerns applications relating to stem cells obtained from embryonic tissue (W0003068937, WO02064755, WO000385831).

The use of human stem cells widely described in prior art entails many problems which are evidence of the strong need to conduct further research in this area. Some of the main obstacles entailed by the use of embryonic cells are ethical questions, the danger of the occurrence of genetic defects as well as the risk of transferring viral and oncogenic diseases. There is thus a strong need for stem cell lines whose use would eliminate the risk of the above obstacles.

Prior art discloses the properties of deer antler tissue which is recognized as the most rapidly growing form of bone among mammalian tissues. Attempts have been made to make use of the proliferative properties of this tissue, especially through the isolation of growth factors. Application W093/19085 discloses a method of isolating a growth factor that is a substance capable of regenerating damaged bone tissue. A method is disclosed of obtaining an extract isolated from the antlers of the Japanese deer (*Cervus nippon*) which stimulates the proliferation of hematopoietic stem cells and megakaryocytes. Application WO 2004/112806 discloses a composition for the treatment of neuronal disorders made from growth hormone markers obtained from deer antlers.

In 2005, the authors of the present invention began to research the growth process of the antlers of the noble deer (*Cervus elaphus*). In those experiments, the MIC-1 stem cell line was derived from the growing deer antlers. The MIC-1 stable cell line was deposited at the DSMZ (Deutsche Sammlurll Von Mikroorganismen Und Zellkulturen, Inhoffenstr. 7 B, D-38124 Braunschweig) under the accession DSM ACC2854 on Jul. 16, 2007. In 2006, a patent application was made, P 378963, whose subjects included the novel stem cell line MIC-1 from growing deer antlers, the use of terminal lateral fragments of growing deer antlers in the production of a stable stem cell line was well as the use of these cells in the reconstruction of bone and cartilage lesions in humans and animals. Currently, one of the main directions of research is the search for sources of a preparation for stimulating regenerative processes in complex organs such as the skin. Research on the physiology of aging and regeneration processes in tissues has led to the discovery of the role of stem cells it these processes.

The goal of the present invention is to deliver a preparation and products based on stem cells, which have a beneficent effect on the regeneration of skin and the reconstruction of its elements.

Unexpectedly, it turned out that this cell homogenate from cells of the MIC-1 stem cell line exhibits particularly beneficial activity in stimulating the growth and regeneration of diseased or damaged elements of the skin.

The subject of the present invention is cell homogenates obtained by the destruction of cells from the MIC-1 stem cell line derived from the growing deer antlers (Cervidae) deposited at the DSMZ under the accession DSM ACC2854.

Preferably, the destruction of the cells and the homogenates is performed using ultrasounds. Destruction of antlerogenic stem cells releases active substances contained therein, which activate regenerative processes.

In a preferable embodiment of the present invention, one unit of the homogenate comprises the extract from 1 million cells.

The next subject of the present invention is a method of obtaining a bioactive cell homogenate, characterized in that cells are cultured and are subsequently separated from the medium, disrupted using ultrasounds, wherein the cells used are cells of the MIC-1 stem cell line derived from growing deer antlers (Cervidae) deposited at the DSMZ under the accession DSM ACC2854.

Preferably, in the method according to the present invention, the cells are cultured on plates or in suspension.

Preferably, in the method according to the present invention, a standardised homogenate is produced which comprises the extract obtained from 1 million cells in one unit.

The next subject of the present invention it is a pharmaceutical or cosmetic composition which comprises an active ingredient and a pharmaceutically permissible carrier, characterized in that the active substance is the homogenate of cells from the MIC-1 stem cell line derived from growing deer antlers (Cervidae) deposited at the DSMZ under the accession number DSM ACC2854.

Preferably, the composition is meant for intradermal or topical application.

The advantages of the present invention are, first of all, standard cell culture conditions and cells with a high proliferation potential, as well as the absence of ethical considerations, which are usually brought up against research on human embryonic cells.

Another subject of the present invention is the use of a homogenate obtained from cells from the MIC-1 stem cell line derived from growing deer antlers (Cervidae) deposited at the DSMZ under the accession DSM ACC2854, in the production of a preparation for the medical and cosmetic treatment skin.

Preferably, the preparation is designed for topical or intradermal application.

The skin, as an enclosing organ, is particularly susceptible to diseases and trauma due to its protective function. Repair processes occur in it throughout life. Due to its biostimulant properties, the extract is useful in broadly defined regenerative medicine and cosmetology. The cell homogenate from cells from the MIC-1 cell line has a beneficial effect on epithelium formation, stimulates the healing of wounds and skin lesions, activates hair follicles, stimulates the production of collagen fibers, augments the proliferation of fibroblasts and activates tissue vascularization. The MIC-1 line stem cell homogenate exhibits properties that influence the regeneration of skin and its biorenewal which it make it possible to reconstruct age-related deterioration. The cell homogenate and preparations made on its basis are widely applicable as anti-wrinkle agents, lifting and anti-aging agents which regenerate skin damaged by solar radiation, revitalize the skin by increasing its tenderness and elasticity, as well as cosmetics for the maintenance of mucous membranes.

Furthermore, the cell homogenate and preparations made on the basis are widely useful as agents for the treatment of difficult to heal wounds arising, for example, as a result of diabetes, shin ulcerations resulting from the vascular disease such as vain disorders, Reno disease, as well as agents for attenuating radiation damage and skin damage following chemotherapy.

The cell homogenate constituting the subject of the present invention and the preparation made on its basis are further useful in aesthetic medicine, dermatology and in sports medicine, particularly as agents for stimulating regeneration following acne, for healing burns and for healing vascular disorders following trauma.

The subject of the present invention is useful in as a biostimulating preparation for the mucous membranes, particularly in relation to paradontosis, mucous membrane ulceration, for example in the oral cavity, the nose and the vagina. The cell homogenate being the subject of the present invention, as well as preparations made of it are also useful in veterinary medicine in the acceleration of healing and hair regrowth.

The next subject of present invention is a new use for the cell homogenate produced using the disruption of cells from the MIC-1 stem cell line derived from growing deer antlers (Cervidae) deposited at the DSMZ under the accession DSM ACC2854 in the production of a preparation for the regeneration of tissue selected from among muscle, nervous and epithelial tissue.

Preferably, the preparation is used in the form of drops for the eyes, an ointment for the eyes, and injectable preparation or a preparation for saturating spongostan.

Preferably, the composition of the eyedrops ecomprises, per milliliter, the homogenate at a rate of 10 U/ml, 50 mg or 10 U/ml 25 mg as well as ancillary substances.

Preferably, the ancillary substances are selected from a group comprising polyvinyl alcohol, disodium hydrogen phosphate, sodium dihydrogen phosphate, sodium chloride, benzalkonium chloride, and water.

Preferably, the eye ointment contains the module at a rate of 10 U/ml 50 mg, an injectable preparation comprises the homogenate at a rate of 10 U/ml 100 mg, and a preparation for saturating spongostan comprises the homogenate at a rate of 10 U/ml 100 mg.

BRIEF DESCRIPTION OF DRAWINGS

The subject of the present invention is shown in the Figures, where FIG. 4A represents an uncovered nerve following 12 weeks of observation, FIG. 4B shows the isolated neuron, visible seams connecting the implants with stubs, FIG. 5 represents a control group 12 weeks, implantation of the ischiadic nerve in the rat.

EXAMPLE 1

Figure 1:
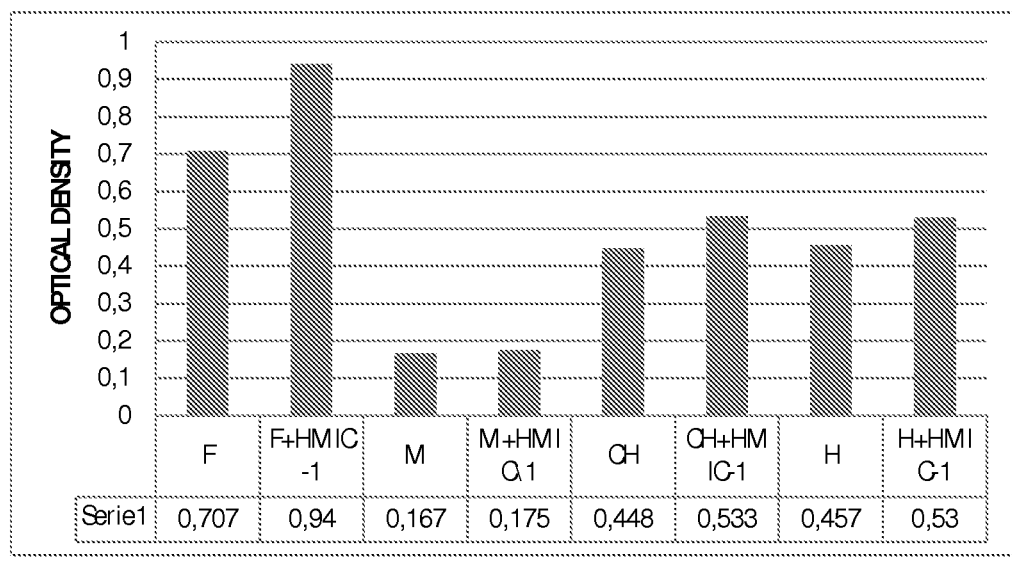
FIG. 1 shows the effect of MIC-1 cell homogenate on the proliferation of: fibroblasts (F), myocytes (M), chondrocytes (CH) and hepatocytes (H). Fibroblasts—MIC-1 homogenate (F+HMIC-1), myocytes–MIC-1 homogenate (M+HMIC-1), chondrocytes–MIC-1 homogenate (CH+HMIC-1), hepatocytes–MIC-1 homogenate (H+HMIC 1)

Production of the Homogenate Containing Mesenchymal MIC-1 Stem Cells from Deer Antlers The culture is maintained in an incubator under standard conditions, at a temperature of +37° C. and an atmosphere containing 5% $CO_2$. Antlerogenic cells are adhesive, and grow in 175 ml flasks (BD Falcon cell culture flask) in MEM culture medium from Cambrex which contains 10% fetal bovine serum, 100 U/ml penicillin and 0.1 mg/ml streptomycin. The efficiency from one bottle is about 30 million cells per 14 day culture cycle. After a full monolayer is obtained, the cells are detached from the flask bottom using 0.05% trypsin with 0.02% ethylenediaminotetraacetic acid (EDTA) and transferred to centrifuge tubes. The tripsin in the centrifuge tubes is inactivated by adding 10 ml of supernatant. The cells are then washed twice in PBS and centrifuged off. Centrifugation is performed in a Heraeus centrifuge for 10 minutes at about 1000 RPM. The supernatant is decanted off a resulting in a cell pellet. This is suspended in 0.9% sodium chloride at a rate of 1 billion cells per 50 ml of liquid. The homogenous suspension is cooled in a water cooled homagenisation chamber to a temperature of about 4° C. In the steel chamber, with continuous cooling, ultrasounds are used at a frequency of 20 kHz for 30 seconds to disrupt the cells (Ultrasonic disintegrator UD-20, Techpan). The solution is scaled in biological units, one unit represents the extract obtained from 1 million cells. The homogenate is stored frozen at −80° C.

EXAMPLE 2

Production of a Form of the Cell Homogenate Containing Mesenchymal Stem Cells MIC-1 from Deer Antlers The preparation based on the cell homogenate may occur in the form of an ointment, cream, tonic or any other form suitable for topical application. The preparation may also have dermal uses. An example of an ointment base is Hascobase or any other known and commonly used ointment base used by specialists such as Lekobaza, anhydrous eucerine, cholesterol ointment or Vaseline (Farmacja stosowana. red. Stanislaw Janicki i Adolf Flebig, PZWL Warszawa 1996). 10 g of suspension containing 50 units of homogenate were supplemented with 40 g of medium. The mixture was homogenized using a semiautomatic mixture, PA 200 Alpine a (Poland). Homogenization was performed over five minutes in a dedicated container, 50 ml volume, on automatic settings.

At tonic was prepared, where 50 ml of 96% ethanol were supplemented with 50 ml of suspension containing 100 biological units of the homogenate. The resulting preparations were stored in cool conditions.

EXAMPLE 3

Examination of the Effect of the Cell Homogenate on the Skin Following a Single Topical or Intradermal Dose The evaluation of the effect of the cell homogenate on the skin following a signle topical or intradermal administration was conducted on 2 of 4 groups containing 6 individuals each selected from a group of 24 white New Zealand rabbits.

During the topical administration, 6 $cm^2$ of depilated, undamaged skin on one side of the rabbit (in the area of the rib cage,) were treated with 0.5 ml of the preparation. The same surface on the other side (control) was treated with the appropriate medium. The site of administration was examined over 96 hours.

During intradermal administration, 6 $cm^2$ of desolated, undamaged skin on one side of a rabbit (in the area of the rib cage) was injected at a marked site intradermally with 0.5 ml of the preparation. The marked site on the other side of the rabbit was injected with 0.5 ml physiological saline, and the condition of the skin was evaluated after 96 hours.

Following the single dose, we observed a slight blushing of the skin starting on the second day of observation, which ended after 10 days. Both forms were tolerated well.

EXAMPLE 4

Evaluation of the Effect of the Cell Homogenate on the Skin Following Multiple Topical and Intradermal Administration The evaluation of the effect of the homogenate cell on the skin following multiple topical or intradermal administration was conducted on 2 of 4 groups containing 6 individuals each selected from a group of 24 white New Zealand rabbits.

During the topical administration, 6 $cm^2$ of depilated, undamaged skin on one side of the rabbit (in the area of the rib cage) were treated with 0.5 ml of preparation, once daily over 28 consecutive days. An identical surface on the other side control was treated with the appropriate medium in the same way as the examined preparation. The administration site was controlled multiple times over the first 8 hours of treatment, and then daily for the next 21 days.

During intradermal administration, 6 $cm^2$ of depilated, undamaged skin on one side of the rabbit (in the area of the rib cage) were treated with 0.5 ml of preparation once daily over 14 consecutive days. The same surface on the other side, control, was treated with an appropriate medium in an identical mode as the exam preparation. The site of administration was controlled multiple times over the first 8 hours of treatment and then daily over the next 21 days.

On the 14th day of observation in 6 animals from the multiple administration groups, we collected skin sections for histological evaluation from locations with intensive hair growth. In 3 animals from the control group, tissue sections from the sites where the physiological saline was administered were collected for histological evaluation. Administration of the homogenate intradermally did not cause any damage to the skin and was well tolerated. In the preparations, we observed an increased number of hairs in the growth phase as compared to the control group, as well as a thickening of the hair around the hair bulb. In the derma, we observed an increased number of collagen fibers. These processes were observed most clearly in the group receiving the MIC-1 cell homogenate intradermally.

The patches of skin which were treated with the cells exhibited faster hair regrowth than areas treated with physiological saline. Visible differences were observed on the 6th day of observation. Complete hairy regrowth to its proper length for a given individual, meaning from 35 to 42 mm, occurred after about 10 to 14 weeks. Hair growth during 2-3 weeks was accelerated and amounted to about 4 mm per week. No noticeable growth was observed in the control group. Subsequently, the growth was 2-3 mm per week. Administration of the homogenate intradermally caused no damage to the skin and was well tolerated. Histological preparations following the application of the homogenate, as compared to the control group, resulted in the considerable growth of secondary hair and an increase in the number of newly synthesized collagen fibers.

EXAMPLE 5

Evaluation of the Effect of an Ointment Based on the MIC-1 Stem Cell Homogenate

The evaluation was performed on 9 rabbits divided into 3 groups of 3 animals each, using 3 types of ointment of various concentrations: 1 U/1 g of Hascobase, 0.5 U/1 g of Hascobase as well as 0.1 U/1 g of Hascobase. Group 1 rabbits were treated with the 1 U/1 g ointment, group 2 was treated with the 0.5 U/1 g ointment and group 3 was treated with 0.1 U/1 g. All groups were treated according to the following procedure: 6 $cm^2$ of depilated, undamaged skin on one side of the rabbit (in the area of the rib cage) were treated with 0.5 ml of preparation once daily over 28 consecutive days. The same surface on the opposite side (control) was treated with the appropriate medium (Hascobase) in the same way as the examined preparation. The site of administration was controlled multiple times during the first 8 hours following administration and then daily over the next 28 days.

No intensified hair growth was observed in the group receiving the 0.1 U/1 g ointment. The group treated with the 0.5 U/1 g ointment. Accelerated hair growth was observed on about the 26 day post application. The largest concentration was active on about the 21st date post application.

We measured blood flow in the skin in rabbits of group 1, both on the treated and controlled sides.

The measurement was made using a laser Doppler flow meter, and MBF3D (Moor Instruments Ltd) and a P4s probe, 0.46 mm in diameter. The device emits monochromatic light at a wavelength of 780-820 nm that is produced by a semiconductor laser, 1.5 mW of power. The Doppler laser method is based on the emission of monochromatic optical radiation into tissues and detection of dispersed light which returns to the surface of the tissue. During the dispersal of light on erythrocytes which are moving, the frequency of the wave changes depending on the speed of the erythrocytes and the angle made by the path of the erythrocytes and the photon (Doppler phenomenon). An appropriate detection device with a signal converter and analyzer makes it possible to collect information regarding the blood saturation of a given tissue, defined as the product of the local blood velocity and the concentration of erythrocytes averaged per the volume of tissue where the light penetrates. Blood flow measurements in one area of the skin spanned a minute. The analysis was performed on the slowest 20 second flow interval. The extent of blood flow, the perfusion, was expressed as the product of the concentration of erythrocytes and their velocity using a relative unit (perfusion unit). A 47% increase of blood perfusion in skin was observed in comparison to control skin.

The use of the ointment on the skin was well tolerated. We observed an insignificant hyper-perfusion in the area of the application, and the more rapid regrowth of hair on the side where the ointment or tonic was used. Wounds at the sites where tissue samples were collected for histology healed much more rapidly than on the control side. Histological analysis demonstrated similar changes as in the group receiving the homogenate as an injection.

EXAMPLE 6

In Vitro Evaluation

In vitro studies showed that the substances contained in the velvet and in deer antler extract stimulate the proliferation of fibroblasts, splenocytes and hematopoietic stem cells. Taking into account the presence of blood vessel muscles in antlers, we also evaluated the effect of the homogenate of antlerogenic cells on fibroblasts (connective and epithelial tissue), smooth muscle cells (muscle tissue), chondroblasts (connective tissue), hepatocytes (epithelial tissue) and neurons (nervous tissue).

For this study, we used the following reference cell lines: mouse embryonic fibroblasts (3T3 Balb/c) and human myocytes from the embryonic aorta (UASMC). The primary chondroblast culture was derived from mechanically disrupted rabbit ear cartilage fragments (white California rabbit female of about 4 kg body weight). To set up the primary hepatocyte culture and neuron culture we used organ fragments collected from a neonatal rat (Wistar), which were mechanically disrupted and incubated in smooth muscle growth medium (Cambrex Bio Science, Walkersville Md. USA). The myocytes were cultured in smooth muscle growth medium, whereas the remaining cell lines in DMEM (Bio Whittaker, Lonza, Verviers, Belgium) within the addition of 10% fetal bovine serum and 1% of a solution containing L-glutamine, penicillin and streptomycin (Sigma-Aldrich, Chemie, Steinheim, Germany). The cultures were maintained at 37° C. in a moist atmosphere containing 5% $CO_2$. The time needed to achieve 70% confluence in a culture flasks (75 ml) was: 5 days for myocytes and neurons, 10 days for fibroblasts and chondroblasts, and 21 days for hepatocytes. The evaluated cells were removed from culture flasks using a solution of 0.25% trypsin-EDTA (Sigma Aldrich) and re-inoculated at 100,000 cells per well on 12 well plates. After 24 hours, the medium was exchanged and a homogenized suspension of MIC-1 cells was added at a dose of 0.2 units (1 biological unit equals the homogenate obtained from 1 000 000 MIC-1 cells). The plates were incubated for 120 hours after which time the cells were photographed and counted using the SRB colorimetric test (where the SRB test determines the number of living cells that bind a die, sulphorhodamine B). The cells were fixed with 50% trichloroacetic acid and then stained with 0.4% SRB in 1% acetic acid for 30 minutes. Unbound dye was removed by rinsing in 1% acetic acid and the died bound to proteins of the cells was extracted with 10 mM unbuffered Tris. Optical density was then read on an Elx-800 plate reader (Bio-Tek instruments, USA) at a wavelength of 562 nm. The sample control consisted of the same medium as used in the procedure. All of the reagents for the tests were purchased from Sigma.

To evaluate the significance of the differences between the individual groups of the results we used the Student's t-test and as statistically significant we accepted $p<0.05$. All statistical analyses were performed using the Statistica 7.1 package from Statsoft.

The biggest increase in proliferation was obtained for fibroblasts and myocytes, because there numbers grew by a respectively 32 and 28%. In the culture of Contra blasts with the homogenate of MIC-1 sells there was a 19% increase in the number of hunger blasts as compared to those cultured without in the addition of the homogeny. A similar situmulating influence of the homogenate was observed on hepatocytes whose number grew by 16% compared to have data sites not treated with it (FIG. 1). These differences were always statistically significant. No increase in the number of cells was observed for neurons treated with the homogenate. After 120 hours of incubation of all cell types with the homogenate they exhibit no signs of aging (shrinkage) as was observed in the case of cells not treated with the homogenate.

The mesenchymal stem cells (MSC) introduced into damaged tissue participate in its regeneration, and after several weeks from administration there remains only a small number of them which leads to the conclusion that the regeneration is the result of factors secreted by the MSC which modulate the microenvironment at the site of the lesion, and in this way inducing the survival and proliferation of in the endogenous host cells. The above-mentioned factors include proteins regulating hematopoiesis, angiogenesis, healing, immune response as well as the mobilization and proliferation of hematopoietic stem cells. A similar mechanism was observed following the administration of antlerogenic stem cells into cartilage lesions in the ear and jawbone in the rabbit. The reconstructed tissues contained concentrations of undifferentiated stem cells, which underwent apoptosis over time. Likewise, the individual studies confirm the influence of the MSC on the survival and secretory activity of other cells. The participation of MIC-1 cells in the regeneration of damaged tissues as well as the described stimulatory influence of the substance contained in antlers on the proliferation of cells and the acceleration of healing of breakages has led us to study the influence of the homogenate of MIC-1 cells on various types of cells in vitro. The results obtained indicate the considerable stimulation of the proliferation of fibroblasts and myoblasts by the homogenate of MIC-1 cells as well as a smaller influence on the proliferation of chondroblasts and hepatocytes. Only for the neurons was there no increase in the observed number during culturing with an addition of the homogenate. Nevertheless, the survivability of cells increased threefold, and the neurons, in addition to increasing their size, developed a dense net of mutual interconnections. Cell cultures with an addition of antlerogenic cell homogenate thereby create new opportunities in regenerative medicine facilitating the possibility of obtaining enough material to fill in lesions in any tissue.

EXAMPLE 7

In Vivo Assay, Epithelial Tissue (Cornea)

Figure 2:
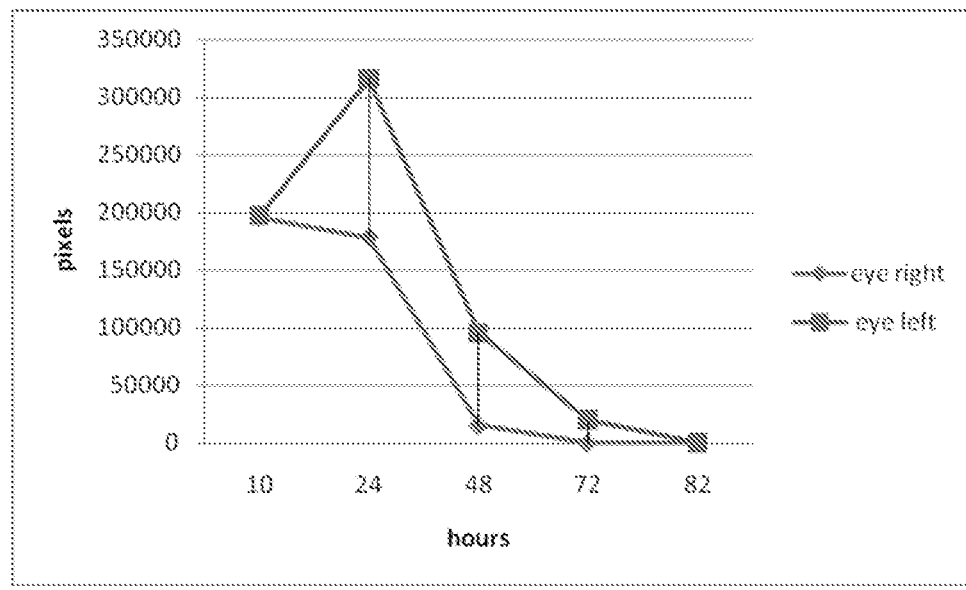
FIG. 2 represents the surface of the lesion in pixels following the use of a drop with a concentration of 0.5 million cells/ml of preparation.
Figure 3:
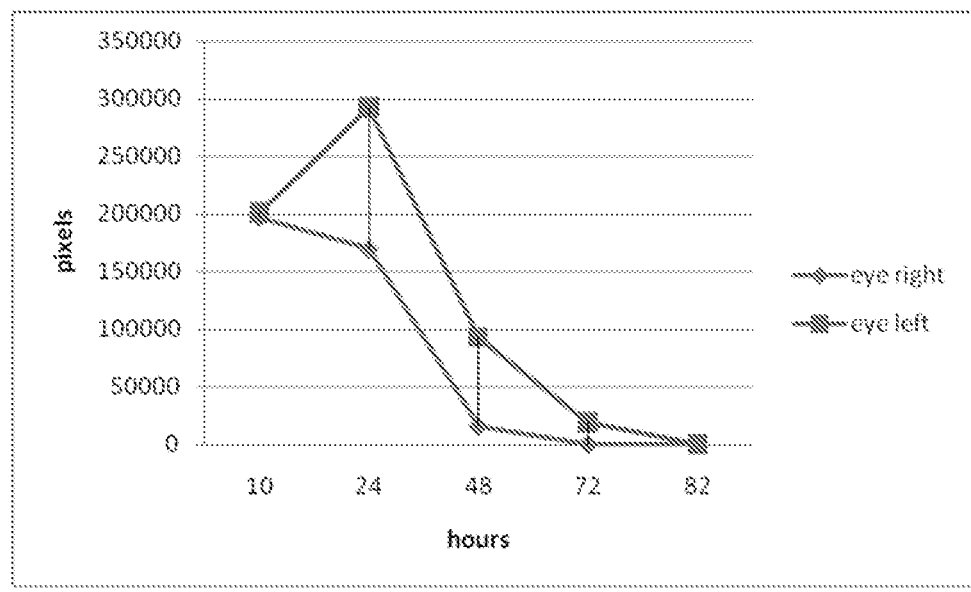
FIG. 3 represents the surface of the lesion in pixels following the administration of a drop with a concentration of 0.5 million cells/ml of preparation

In this study we used 12 rabbits, young 8-month females of the New Zealand white variety, weighing from 2.5 to 2.9 kg. During the experiment, the animals were kept in individual cages with unlimited access to food and water in a 12 hours light:12 hours dark cycle. Prior to beginning the experiment, all of the rabbits had their eyes examined so as to eliminate any extant disorders of the cornea or the conjunctiva as well as the remaining structures of the anterior eyeball (anterior chamber and iris). We conducted a fluorescein assay (evaluation of the anterior portion following the administration of a 2% fluorescein solution to the conjunctiva using a cobalt filter) and evaluation using the slot lamp. No irregularities were observed. In each animal, one eye was examined and the other eye constituted the control. The abrasion of the corneal epithelium was performed in the following way. After local anaesthesia with a solution of Alcaine (proxymethacaine hydrochloride, 5 mg/ml, Alcon) the corneal epithelium was damaged in both eyes of each rabbit through the application of a disk, 3 mm across, of Whatman #1 tissue soaked in n-heptanol (Sigma Aldrich). The disc was applied to the center of the cornea and left in place for 30 seconds following its removal the eye was rinsed with isotonic saline, 0.9% NaCl. Throughout the experiments, in 6 rabbits, the right eyes (experimental eye) were treated 3 times per day at equal intervals (every 8 hours) until the last day with the homogenate at a concentration of 0.5 U/ml (number 1 eyedrops) (3 eyes) and 0.25 U/ml (number 2 eyedrops) (3 eyes) at a rate of 3 drops. One biological unit equals the homogenate obtained from 1 000 000 MIC-1 cells, which corresponds to 1 mg of cell mass placed in 100 mg of distilled water. The left eye, constituting the control, was treated in the same pattern and volume using the medium. In another 6 rabbits, we used the homogenate in the form of an ointment in the same concentration as the drops. These were administered in the same patterns to each eye, in the form of a lump of ointment the size of a peppercorn. The evaluations encompassed corneal damage and the rate of its regeneration in the examined group (2×6 animals) in comparison to the control. To evaluate the rate of healing of lesions in the eye in the rabbits, the eyes were stained with a 2% solution of fluorescent and examined with a 10 hour interval between the damage and the initiation of the measurements. This time corresponds to the lag phase in the healing of the cornea observed in vivo. The eyes were examined using a slot lamp, and we also performed the fluorescent assay and photographs (photographic documentation) on all of the experimental and control corneas. The photographs were made during every 10 hours post trauma. The surface of the damaged area of the cornea was measured in pixels, analyzing the size of the lesion using the Adobe Photoshop CS Extended package. The results obtained were averaged to evaluate the decrease of the wound surface over time. The experiment terminated with the acquisition of 100% wound closure in the cornea in both groups, both the experimental and control. The results were gathered in Table 1 as well as FIG. 2 demonstrating the surface of the damage in pixels following the administration of a drop with a concentration of 0.5 million cells/ml of preparation, Table 2 and FIG. 3 represent the data for the damage surface in pixels following the administration of the ointment at a concentration of zero decimal 5 million cells/ml of preparation.

TABLE 1

| time | Right eye | | Left eye | |
|---|---|---|---|---|
| | average | SD | average | SD |
| 0 | | | | |
| 10 | 195735 | 11690 | 197212 | 4883 |
| 24 | 178169 | 10004 | 316094 | 15551 |
| 48 | 15175 | 981 | 95291 | 5462 |
| 72 | 0 | | 19987 | 1885 |
| 82 | 0 | | 0 | |

TABLE 2

| time | Right eye | | Left eye | |
|---|---|---|---|---|
| | average | SD | average | SD |
| 0 | | | | |
| 10 | 196968 | 11639 | 201174 | 8293 |
| 24 | 169675 | 12902 | 292304 | 13688 |
| 48 | 16110 | 4860 | 92942 | 12295 |
| 72 | 0 | | 19133 | 2534 |
| 82 | | | | |

In all eyes which were treated with the preparation (drops or ointment) containing the MIC-1 homogenate, the healing occurred much more rapidly. In the first 24 hour period after the treatment no increases were observed in the damaged areas. Complete healing occurred before the lapse of 72 hours of observation. The beneficial influence of both preparations was approximately equal. The preparations with a lower concentration of homogenate exhibited an efficacy decreased by about a third.

EXAMPLE 8

In Vivo Assay, Nervous Tissue (a Ski Attic Nerve)

Figure 6:
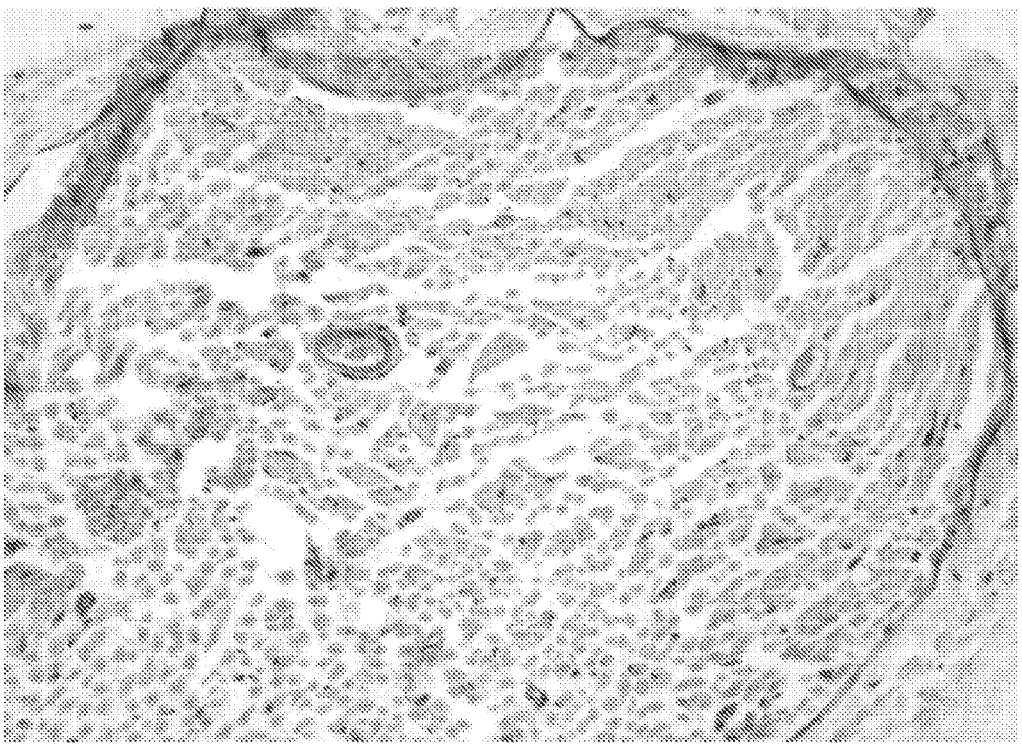
FIG. 6 represents the control group following 12 weeks, implantation of the ischiadic nerve in the rat.
Figure 7:
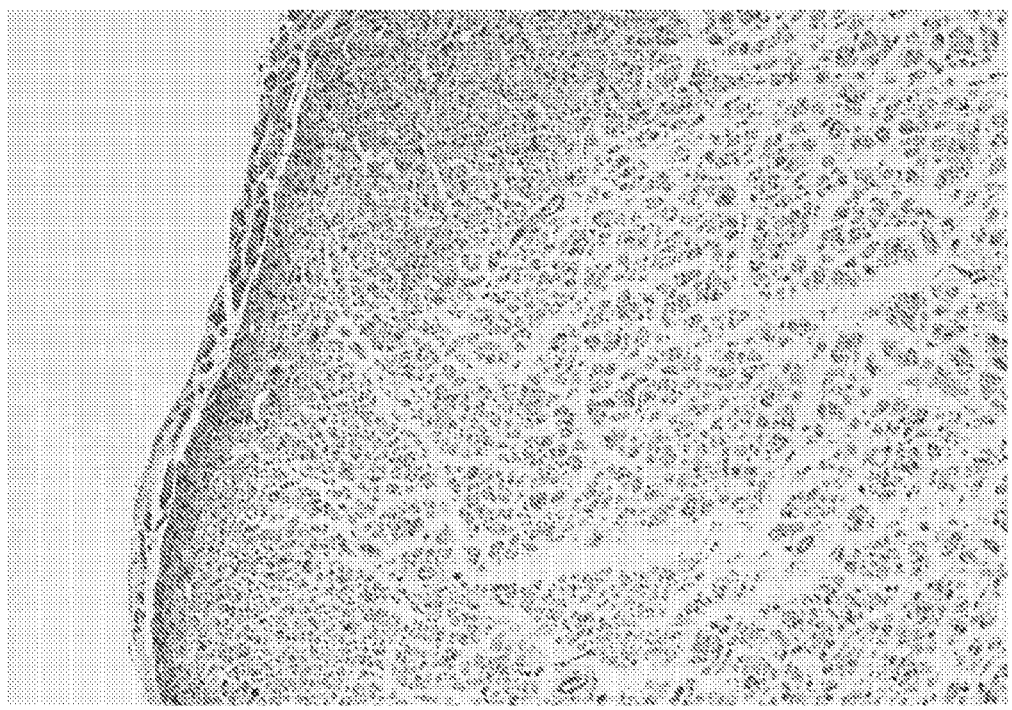
FIG. 7 represents the experimental group following 12 weeks, peripheral regeneration of the implant.
Figure 8:
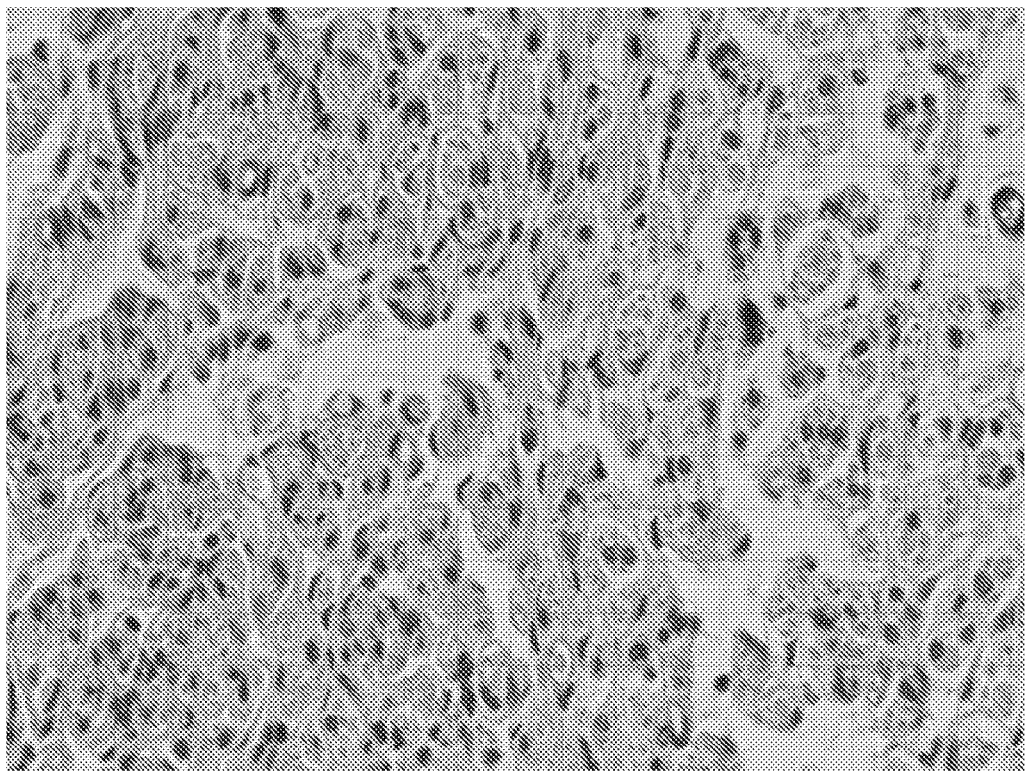
FIG. 8 represents the experimental group 12 weeks following the operation, peripheral regeneration of the implant.
Figure 9:
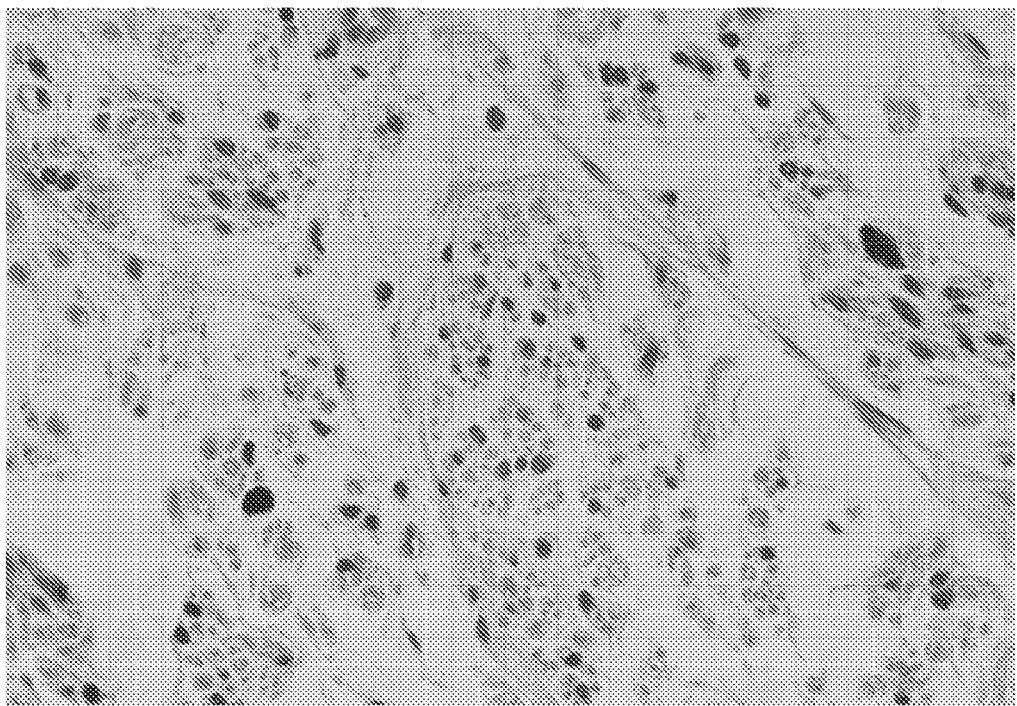
FIG. 9 shows the experimental groups following 12 weeks, nervous fibers in the center of the implant.

In these experiments we used young (2 to 3-month-old) Wistar rats of both sexes, weighing from 240 to 310 grams During the experiment, the animals were maintained in cages with unlimited access to water and food in a light/dark cycle of 12:12. The experimental group consisted of 4 animals and the control group of 3 animals (1 rat died during the experiment, failed to wake from anesthesia). The animals were operated under full anaesthesia with an intraperitoneal injection of ketamine and xylazine at a dose of 75/5 mg/kilograms body weight. We operated using a microscope and microsurgery tools under as septic conditions. Following depilation and desinfection with Octenisept ((Schulke&Meyr GmbH, Norderstedt, Germany), the area was surrounded with sterile tissue. The incision of about 2.5 cm was made lengthwise on the external portion of the thigh. After separating the layers of the thigh muscles, blunt tools were used to make the ischiatic nerve visible, which is located between the rear and interior thigh muscles and the shank of the thigh bone. The nerve was freed over a length of 1.5 cm and a 1 cm fragment of its axis was cut out. The excised portion of the nerve was reimplanted, connecting both stubs at both ends by applying two non-dissolving epineural sutures of 4/0 nylon monofilament MEDICO (SHJIAZHUANG) INDUSTRIES AND TRADE CO., LTD. underneath the implant, we placed a flake of Spomgostan, an absorbable gelatin sponge produced by Johnson & Johnson, Warsaw Poland, sized 1 by 0.5 cm which had been saturated with the cell homogenate at a concentration of one unit per 1 mm of 0.9% NaCl. The incision was sutured as a monolayer, the skin was again disinfected would have walked on a set and left uncovered. In the control group weaves on the spam soaked only with 0.9% NaCl. The postoperative recovery and all animals was correct the wounds healed with primary adhesions and the skin suture was removed on the 7th day following the procedure. We observed a markedly more rapid healing of wounds in the experimental group. After 12 weeks the animals were sacrificed by the administration of thiopental added at a rate of 120 mg/kg. Microsurgery was used to isolate the nerve that had been operated on, collecting its fragment which encompassed the proximal fragment, the implant and the distal fragment (FIGS. 4A and 4B). The isolated implant was divided into 3 parts and placed in a 4% solution of buffered formalin. Comparing the results from the control group (FIGS. 5, 6) and the experimental group (FIGS. 7, 8, 9), the significant difference of the regeneration of the nerve in that implant pertained to the periphery of the nerve fiber but the bundle at the sites were the gelatin sponge saturated with MIC-1 cell homogenate was placed. At the sites we observed the activation and stimulation of pairing mural cells and an increased number of fine blood vessels. Peripherally, in the nerve bundles there are many myelinated and unmyelinated axons, which are evidence of the process of the restitution the continuity of nerve fibers (FIGS. 7, 8). In the central portions of the implants there are less frequent myelinated axons (FIG. 9).

EXAMPLE 9

In Vivo of Valuation. Muscle Tissue (Triceps)

Figure 10:
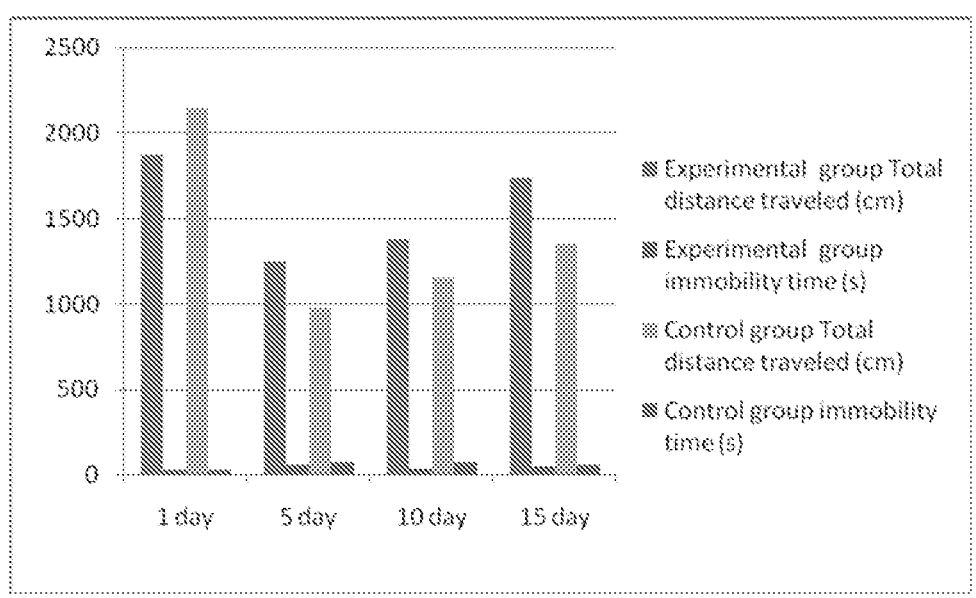
FIG. 10 shows the path length in centimeters and rest time in seconds of a mouse following 180 s of video recording.
Figures 11A, 11B, 11C, 11D:
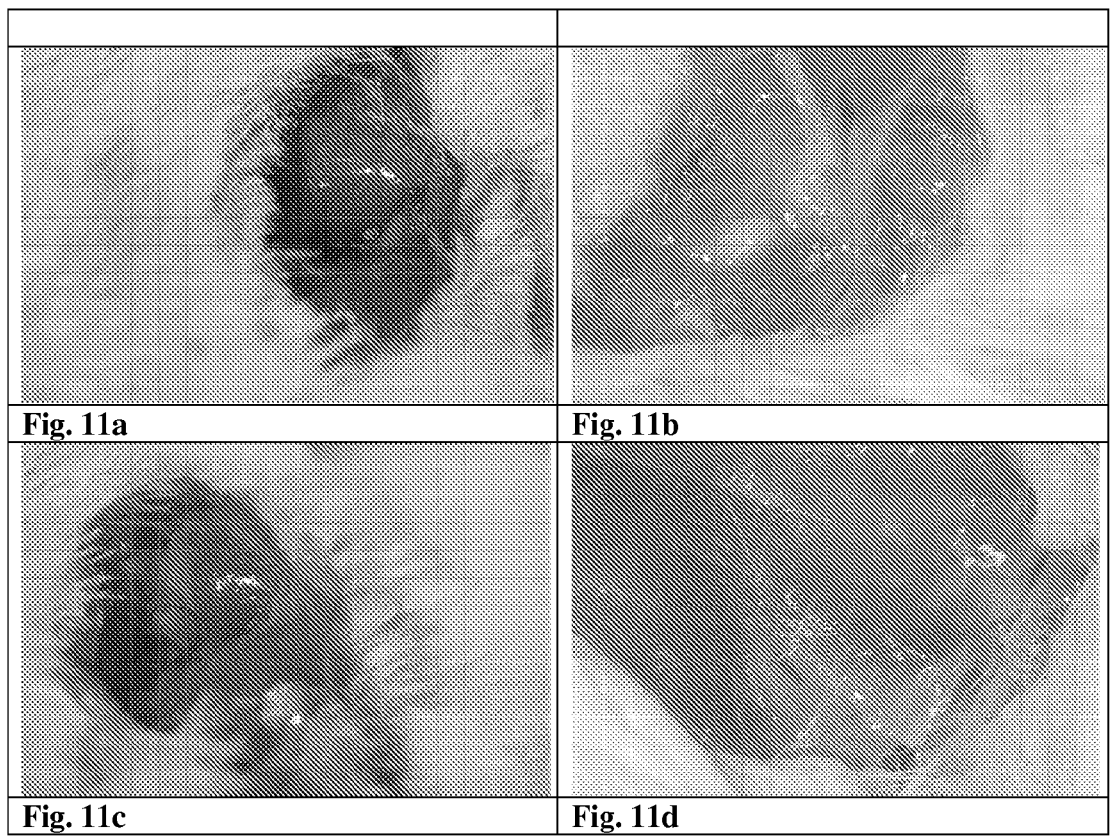
FIG. 11A shows an image of the muscle immediately following the lesion.
FIG. 11B represents an image of the muscle following 14 days after the use of the homogenized.
FIG. 11C shows an image of the muscle immediately following the lesion.
FIG. 11D shows an image of the muscle following 14 days of the use of the medium.
Figure 12A:
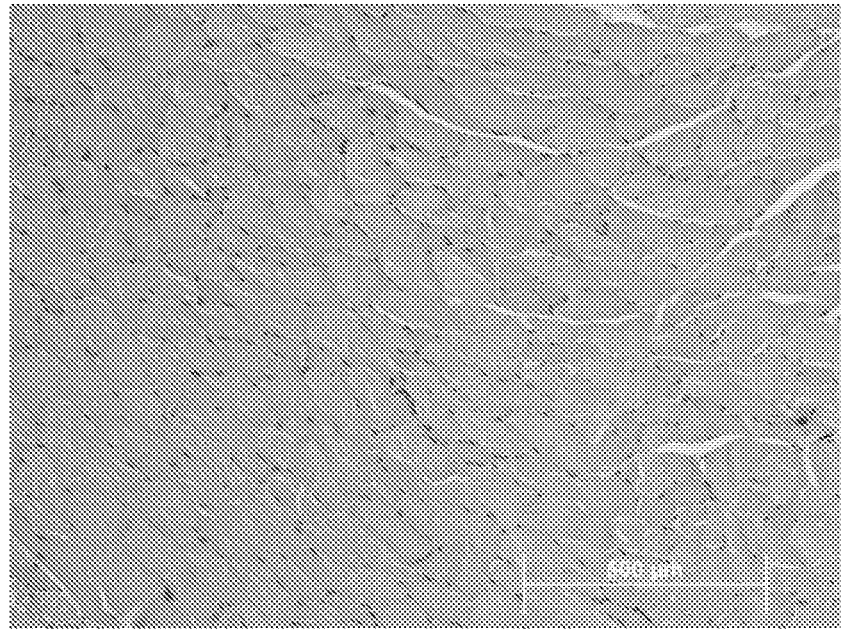
FIG. 12A shows an animal from the experimental group: image of an almost unchanged skeletal muscle—final stages of healing.
Figure 12B:
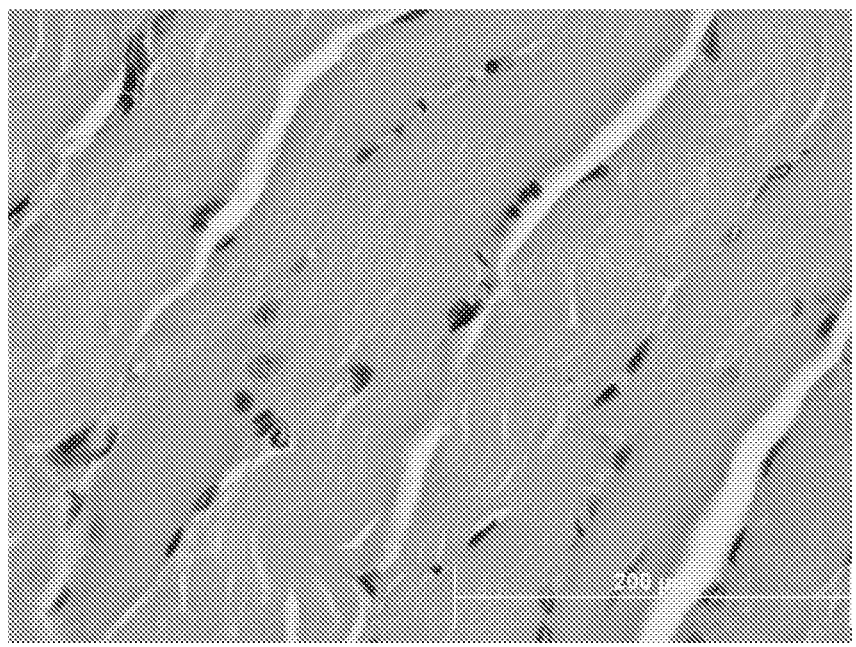
FIG. 12B shows the experimental group, fully regenerated skeletal muscle, lengthwise cross-section. The lesion that had been incurred is confirmed by individual nuclei located in the central portion of the muscle fibers.
Figure 13A:
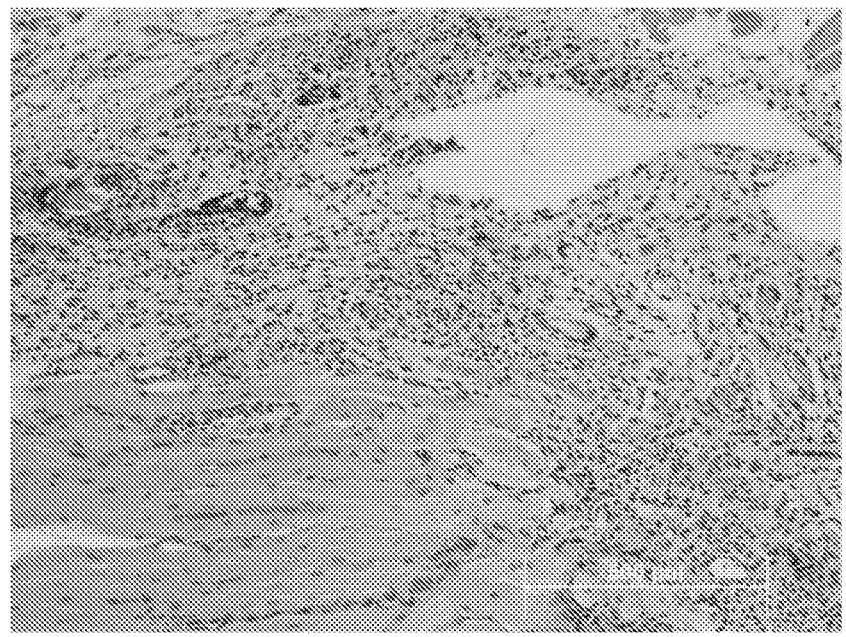
FIG. 13A represents the control group where myotubes and a forming scar are visible after the tissue was crushed.
Figure 13B:
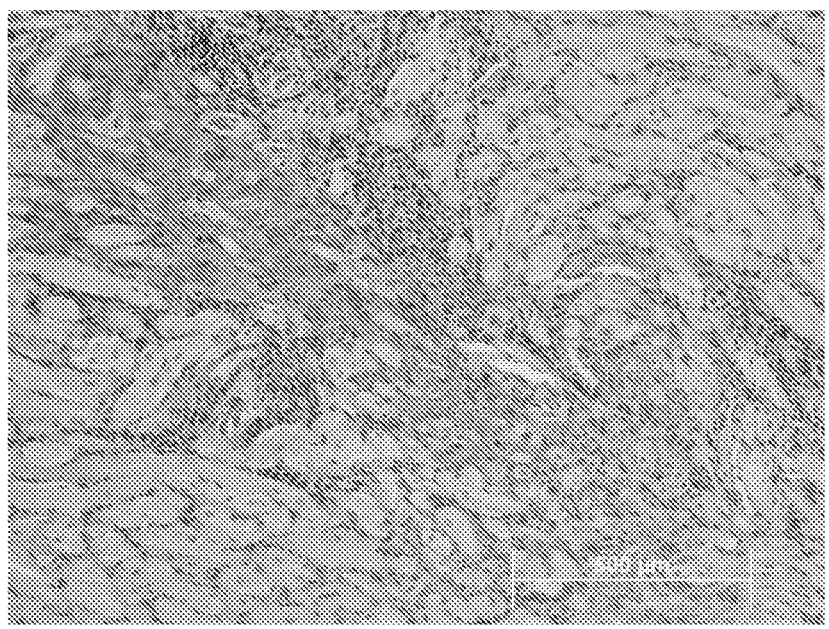
FIG. 13B represents an animal from the control group, regenerating damaged muscle, at the center there is a visible scar with resorbing tissue and giant cells.
Figure 14A:
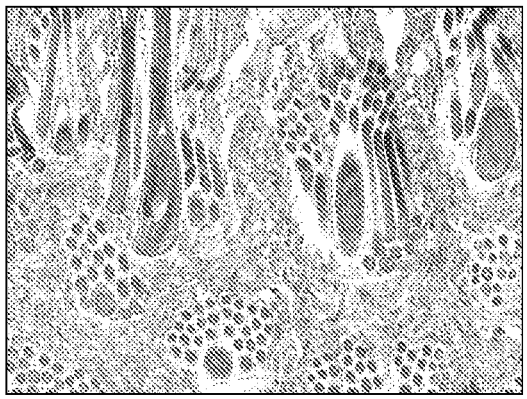
FIG. 14A represents a tangential section of the skin following a 21 day application of dermal homogenate, visible is an increased number of secondary hairs in hair follicles as well as numerous present bundles of collagen fibers.
Figure 14B:
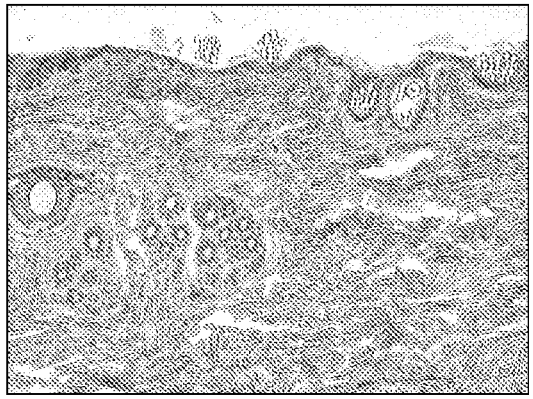
FIG. 14B represents a control tangential section of skin following 21 days application of physiological saline (control)
Figure 15:
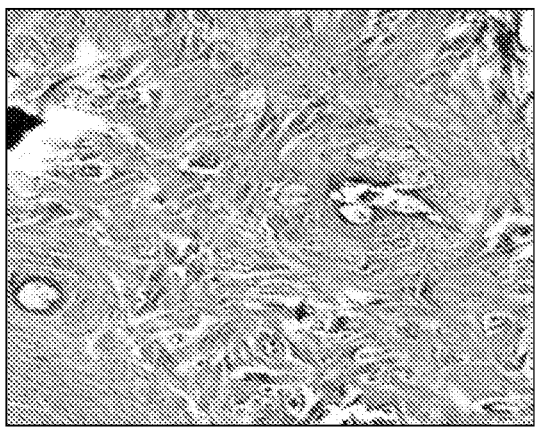
FIG. 15 represents a parallel section of the derma following 21 day application of intradermal homology. Van Gieson staining shows newly formed collagen fibers.
Figure 16:
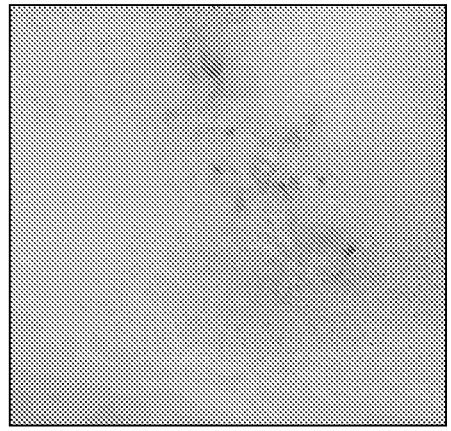
FIG. 16 shows the wound that had healed in the fifth 24-hour period following the isolation of a tissue section which encompassed all layers of the skin, The subject of the present invention as also shown in example embodiments which do not limit the scope of its protection.

In this experiment we used a young, 3-month-old BALB/c mice weighing 18 to 22 g each. The animals were divided into 2 groups of 4 mice, and experimental and a control group. Mice from both groups were operated under anesthetic (intraperitoneal ketamine and xylazine at a rate of 50/5 mg/kg). After shaving and disinfecting the skin with Octenisept, the lengthwise incision uncovered the fine muscles. The hamstring was damaged by crushing an area of about 3×3×3 mm for 30 seconds with surgical calipers with a pressure of about 80 kg/cm². The skin was sutured as a monolayer and the wound was disinfected with Octenisept and left uncovered. The animals from the experimental group were given 7 doses of 0.5 ml of cell homogenate at a concentration of 1 U/ml of preparation in the area of the incurred lesion. The first intramuscular injection was performed immediately following the crushing and then at 48 hour intervals. In the control group, in the same pattern, we used water for the injection. The healing always occurred correctly. The sutures were taken out on the 7th day following the surgery. We observed a markedly more rapid regeneration of the wounds in the experimental group over 2 weeks, as evaluated using the locomotor activity of the mice. For this purpose we used the Smart 2.5.20 package (on the 5th, 10th and 15th day following the surgery). Table 3 and FIG. 10 show the length of the pathway in centimeters and the rest time in seconds of mice during 180 seconds of video recording.

TABLE 3

|  | Experimental group | | Control group | |
| --- | --- | --- | --- | --- |
|  | Path length | Rest time | Path length | Rest time |
| Initial data | 1875 | 32 | 2146 | 30 |
| 5 day | 1250 | 61 | 980 | 75 |
| 10 day | 1380 | 34 | 1154 | 77 |
| 15 day | 1740 | 48 | 1352 | 58 |

By the same token, we observed that there was higher locomotor activity and shorter rest times in animals receiving homogeny injections. After 2 weeks (on the 15th day) we collected a fragment of the muscle from the regenerating area to evaluate it histologically. During the preparation, we microscopically observed that the damaged areas in the experimental group were smaller in every case than in the control group (FIG. 11A-11D). These observations confirmed that the behavioral study results. The collected fragments were placed in 4% buffered formalin. They were used to prepare histological slides. Compared to the control group, in all animals receiving the homogenate in the lesion site we observed a complete regeneration (FIGS. 12A, 12B, 13A, 13B).

The in vitro and in vivo experiments confirm unequivocally the beneficial effect of the homogenate on the regenerateive processes in all tissues. This preparation should thus find many uses as a universal agent for stimulating the regeneration of tissues and organs. It is worth the of mentioned that these processes occur without scarring.

The invention claimed is:

1. A method of obtaining a bioactive cell homogenate comprising disrupting cells separated from media with ultrasound, wherein the cells are cells of MIC-1 stem cell line derived from growing deer antlers (Cervidae) deposited at the DSMZ under the accession number DSM ACC2854.

2. The method according to claim 1, further comprising culturing the cells in a plate or suspension culture.

3. The method according to claim 1, further comprising producing a homogenate titer which comprises the extract obtained from 1 million cells in one unit.

4. A pharmaceutical or cosmetic composition comprising: an effective amount of a homogenate produced from cells of the MIC-I stem cell line derived from growing deer antlers (Cervidae) deposited at the DSMZ under the accession DSM ACC2854, and an ointment base.

5. The composition according to claim 4, wherein the active ingredient is a homogenate comprising extract from 1 million cells.

6. The composition according to claim 4, for topical or intradermal administration.

7. The composition of claim 4, which is a pharmaceutical or cosmetic composition.

8. A method for the regeneration of tissue selected from among nervous, epithelial and muscle tissue in a subject in need thereof comprising administering to the subject the composition of claim 7.

9. A method for saturating spongostan in the eye of a subject comprising administering to the subject the composition of claim 4.

10. The method according to claim 9, wherein the composition is in the form of eye drops or an eye ointment comprising the homogenate at a concentration of 0.5 U/ml to 0.25 U/ml, wherein U unit is a unit of homogenate obtained from 1 million cells.

11. The method according to claim 10, wherein the composition further comprises polyvinyl alcohol, disodium hydrogen phosphate, sodium dihydrogen phosphate, sodium chloride, benzalkonium chloride, water or a combination thereof.

\* \* \* \* \*